US008317327B2

(12) United States Patent
Cleveland et al.

(10) Patent No.: US 8,317,327 B2
(45) Date of Patent: Nov. 27, 2012

(54) SYSTEM AND METHOD FOR EYEBALL SURFACE TOPOGRAPHY AS A BIOMETRIC DISCRIMINATOR

(75) Inventors: Dixon Cleveland, Annandale, VA (US); Arthur W. Joyce, III, Vienna, VA (US)

(73) Assignee: LC Technologies, Inc., Fairfax, VA (US)

( * ) Notice: Subject to any disclaimer, the term of this patent is extended or adjusted under 35 U.S.C. 154(b) by 0 days.

(21) Appl. No.: 11/376,182

(22) Filed: Mar. 16, 2006

(65) Prior Publication Data
US 2006/0210122 A1 Sep. 21, 2006

Related U.S. Application Data

(60) Provisional application No. 60/661,961, filed on Mar. 16, 2005.

(51) Int. Cl.
*A61B 3/14* (2006.01)
(52) U.S. Cl. ...................................... 351/209; 340/5.82
(58) Field of Classification Search .................. 351/205, 351/206, 209, 212; 382/115; 340/5.82; 713/186
See application file for complete search history.

(56) References Cited

U.S. PATENT DOCUMENTS

| | | | |
|---|---|---|---|
| 3,864,030 A | | 2/1975 | Cornsweet ........................ 351/7 |
| 4,641,349 A | * | 2/1987 | Flom et al. ..................... 382/117 |
| 4,836,670 A | * | 6/1989 | Hutchinson .................. 351/210 |
| 5,204,703 A | * | 4/1993 | Hutchinson et al. .......... 351/210 |
| 5,231,674 A | | 7/1993 | Cleveland et al. ................. 382/6 |
| 5,644,642 A | * | 7/1997 | Kirschbaum ................. 382/103 |
| 5,873,832 A | * | 2/1999 | Maloney et al. .............. 600/473 |
| 5,963,300 A | | 10/1999 | Horwitz ......................... 351/209 |
| 2001/0054149 A1 | * | 12/2001 | Kawaguchi et al. .......... 713/175 |
| 2003/0098954 A1 | * | 5/2003 | Amir et al. .................... 351/210 |
| 2003/0123027 A1 | * | 7/2003 | Amir et al. .................... 351/209 |
| 2003/0144650 A1 | * | 7/2003 | Smith .............................. 606/5 |
| 2003/0169213 A1 | * | 9/2003 | Spero ............................... 345/7 |
| 2005/0175218 A1 | * | 8/2005 | Vertegaal et al. ............. 382/103 |

* cited by examiner

*Primary Examiner* — James Greece
(74) *Attorney, Agent, or Firm* — John R. Kasha; Kasha Law LLC (57) ABSTRACT

An embodiment of the present invention is a system for identifying a user by observing irregularities on the surface of an eyeball of the user includes a topography system and a gaze tracking system. The topography system obtains one or more discernable features of the eyeball and stores the one or more discernable features. The gaze tracking system observes the irregularities, compares the irregularities to the one or more discernable features, and identifies the user if the irregularities and the one or more discernable features match.

22 Claims, 10 Drawing Sheets

SYSTEM AND METHOD FOR EYEBALL SURFACE TOPOGRAPHY AS A BIOMETRIC DISCRIMINATOR

This application claims the benefit of U.S. Provisional Application No. 60/661,961, filed Mar. 16, 2005, which is herein incorporated by reference in its entirety.

BACKGROUND

1. Field of the Invention

Embodiments of the present invention relate to systems and methods for using eyeball surface topography as a biometric discriminator. More particularly, embodiments of the present invention relate to systems and methods for using the exterior surfaces of the cornea or sclera as a biometric discriminator and a gaze tracking system to initially and continuously verify the identity of a user using these exterior surfaces.

2. Background of the Invention

Biological processes are not deterministic. Although most people have ten fingers and ten toes, the ridges and groves that populate the surface of these digits are unique to the individual. Since fingerprints are probably the most commonly known biometric, other biometrics are often referred to as biometric fingerprints. Other measures, such as the lengths of the fingers and toes, have been proposed as biometric discriminators. The list of unique patterns that have been used or proposed as biometrics is vast, from the ridges of the ears to the blood vessels on the retinas to the bite pattern of the teeth to the features of the irises.

The term biometric has evolved in the prior art. In U.S. Pat. No. 6,601,956 the term is used to indicate just the measurement of the biological system. More recently the term has been used to include the concept of biometric discrimination; that is the ability to differentiate one person from some or all other persons. Unless otherwise noted, this second meaning of the term is used herein.

DNA is considered the "gold standard" of biometric differentiation, but is invasive and time consuming, making it a poor choice for personal identification for such applications as building access or ATM (automatic teller machine) use. Finger prints are generally believed to differentiate one person from all others. However, like most biometric discriminators, the size and quality of the sample yield the degree of separation. For full differentiation, a 10-point fingerprint match is required; that is 10 features within the fingerprint pattern must match the exemplar. A partial fingerprint with only 5 matching features might only exclude 80% of the population from the matching group. Such weak differentiation can only be used for very casual security or it must be paired with other biometric discriminator to effectively provide positive identification.

Iris recognition and retinal scans have similar limitations. The quality of the sample, the discernable features and the distribution of the population are all factors in the likelihood that the biometric sample can differentiate between an individual and the rest of the population.

In view of the foregoing, it can be appreciated that a substantial need exists for systems and methods that can advantageously improve the quality of the sample and increase the number of discernable features in biometric discrimination systems.

BRIEF SUMMARY OF THE INVENTION

One embodiment of the present invention is a system for identifying a user by observing irregularities on the surface of an eyeball of the user. This system includes a topography system and a gaze tracking system. The topography system obtains one or more discernable features of the eyeball and stores the one or more discernable features. The gaze tracking system observes the irregularities, compares the irregularities to the one or more discernable features, and identifies the user if the irregularities and the one or more discernable features match.

Another embodiment of the present invention is a method for identifying a user by observing irregularities on the surface of an eyeball of the user using a topography system and a gaze tracking system. One or more discernable features of the eyeball are obtained using the topography system. The one or more discernable features are stored using the topography system. The irregularities are observed using the gaze tracking system. The irregularities are compared to the one or more discernable features using the gaze tracking system. The user is identified using the gaze tracking system if the irregularities match the one or more discernable features.

DETAILED DESCRIPTION OF THE INVENTION

An embodiment of the present invention uses the exterior surfaces of the eyeball, both the cornea and the sclera, to provide positive identification of an individual.

An embodiment of the present invention shows the synergies between the problem at hand and current eye gaze tracking technologies.

An embodiment of the present invention shows how a detailed knowledge of the corneal surface can be used to improve the accuracy of gaze tracking equipment.

An embodiment of the present invention teaches that the surfaces of an individual's eyeballs are unique and can be used as a biometric.

It has long been known that the angular orientation of the optical axis of the eye can be measured remotely by the corneal reflection method. The method takes advantage of the eye's properties that the cornea is approximately ellipsoidal over about a 35 to 45 degree cone around the eye's optic axis, and the relative locations of the pupil and a reflection of light from the cornea change in proportion to eye rotation. The corneal reflection method for determining the orientation of the eye is described in U.S. patent application Ser. No. 3,864,030, for example, which is incorporated by reference herein.

Generally, systems used to measure angular orientation of the optical axis of the eye by the corneal reflection method include a camera to observe the eye, a light source to illuminate the eye, and a processor to perform image processing and mathematical computations. An exemplary system employing the corneal reflection method is described in U.S. Pat. No. 5,231,674, which is incorporated by reference herein. A system employing the corneal reflection method is often referred to as a gaze tracking system.

Another embodiment of the present invention includes a gaze tracking system that uses both the pupil center and corneal reflection, often referred to as the pupil-center-corneal-reflection (PCCR) method. If the illuminator is located coaxially with the camera's optical axis, the eye image has a "bright pupil" effect, and if the illuminator is located off-axis, the eye image has a "dark pupil" effect. One skilled in the art recognizes that eye trackers have many embodiments, and the scope of this invention is not limited to specific types of eye trackers.

The corneal surfaces of people's eyes have small irregularities that are unique to the individual. These irregularities constitute the equivalent of a corneal-surface "finger print" that may be used for biometric identification. The surface of the sclera, which does not have to be smooth at all in order for the eye to form a well-focused image, can also be observed and measured for biometric purposes.

Figure 1:
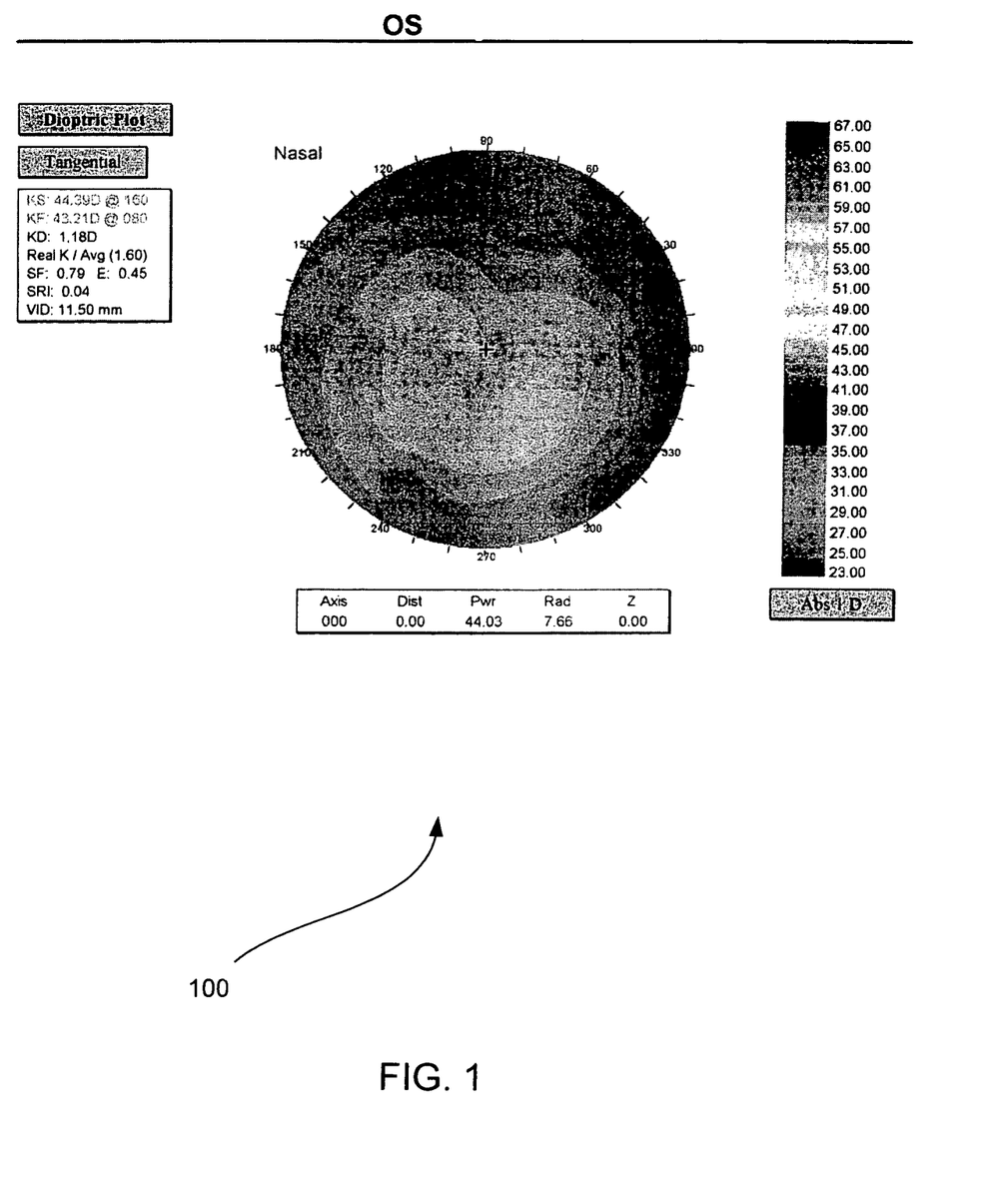
FIG. 1 is an exemplary left eye plot of corneal surface topography produced by corneal topography measurement equipment, in accordance with an embodiment of the present invention.

FIG. 1 is an exemplary left eye plot 100 of corneal surface topography produced by corneal topography measurement equipment, in accordance with an embodiment of the present invention.

Figure 2:
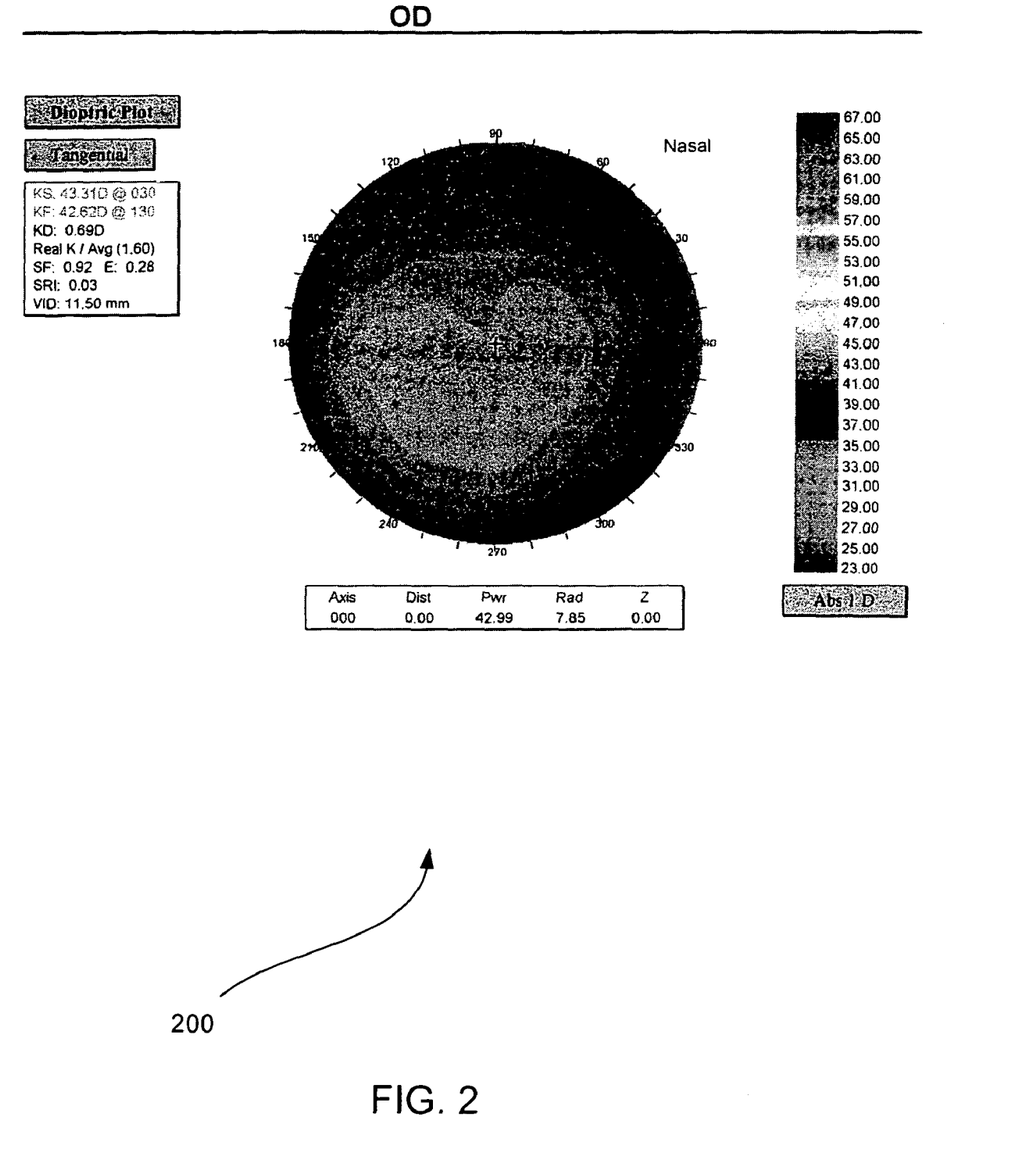
FIG. 2 is an exemplary right eye plot of corneal surface topography produced by corneal topography measurement equipment, in accordance with an embodiment of the present invention.

FIG. 2 is an exemplary right eye plot 200 of corneal surface topography produced by corneal topography measurement equipment, in accordance with an embodiment of the present invention.

Originally, detailed shape data for an individual cornea is typically obtained from a 1-minute test on corneal topography measurement equipment, such as that used by ophthalmologists. An exemplary corneal topography system is the Humphrey® ATLAS™ from Carl Zeiss, Inc.

The output of a corneal topography system is shown in FIGS. 1 and 2. The surface shape is expressed in terms of curvature (diopters), and different curvatures are indicated in the charts by shading levels.

FIGS. 1 and 2 illustrate several key characteristics of corneal topography. First, the general ellipsoidal shape of the cornea, approximately spherical in the middle with a flattening toward the edges, can be seen by the roughly constant 30 diopter curvature in the middle region and the decreasing curvature values toward the outside. In this respect, both of this person's eyes are very similar.

Secondly, the differences between the two eyes, as seen from the shapes of the curvature contours, are apparent. If the surfaces were ideally ellipsoidal, the contour lines would be circular and centered around the center of the cornea. The variations in the curvature contours distinctly highlight the regional protrusions, flat spots, ridges and valleys of the corneal surface topography.

Although the corneal surface is typically measured by observing surface reflections, it can also be measured by optical means. The most sophisticated measurement apparatus use what's referred to as wavefront analysis in which the full optical path is measured. An exemplary wavefront analyzer is the Zywave® II Wavefront Aberrometer from Bausch & Lomb. Such an instrument could be used for the biometric discrimination disclosed in this invention. U.S. Pat. No. 5,963,300 teaches the bright pupil effect, used in some gaze tracking systems, which produces exactly the wavefront exiting the eyeball that a wavefront analyzer needs. So measuring the internal structure of the eye becomes another possible biometric discriminator.

Similarly, iris recognition is used as a biometric discriminator. Measuring the optical distortion of the iris image could be used to infer the optical properties and therefore the surface topography of the cornea. Since it is possible to continually observe the iris, this method may serve as a good means of measuring the surface on a continuous basis.

Another embodiment of the present invention is a method for continuous verification of a computer user's identity with no interference to his work. Additional embodiments exploit gaze tracking equipment that already exists at the workstation.

For the eye to form high-acuity images on its retina, the ideal shape of its corneal surface is ellipsoidal and perfectly smooth. This ideal corneal shape is nearly spherical at the center with a small amount of flattening toward the edges where the cornea meets the sclera.

Figure 3:
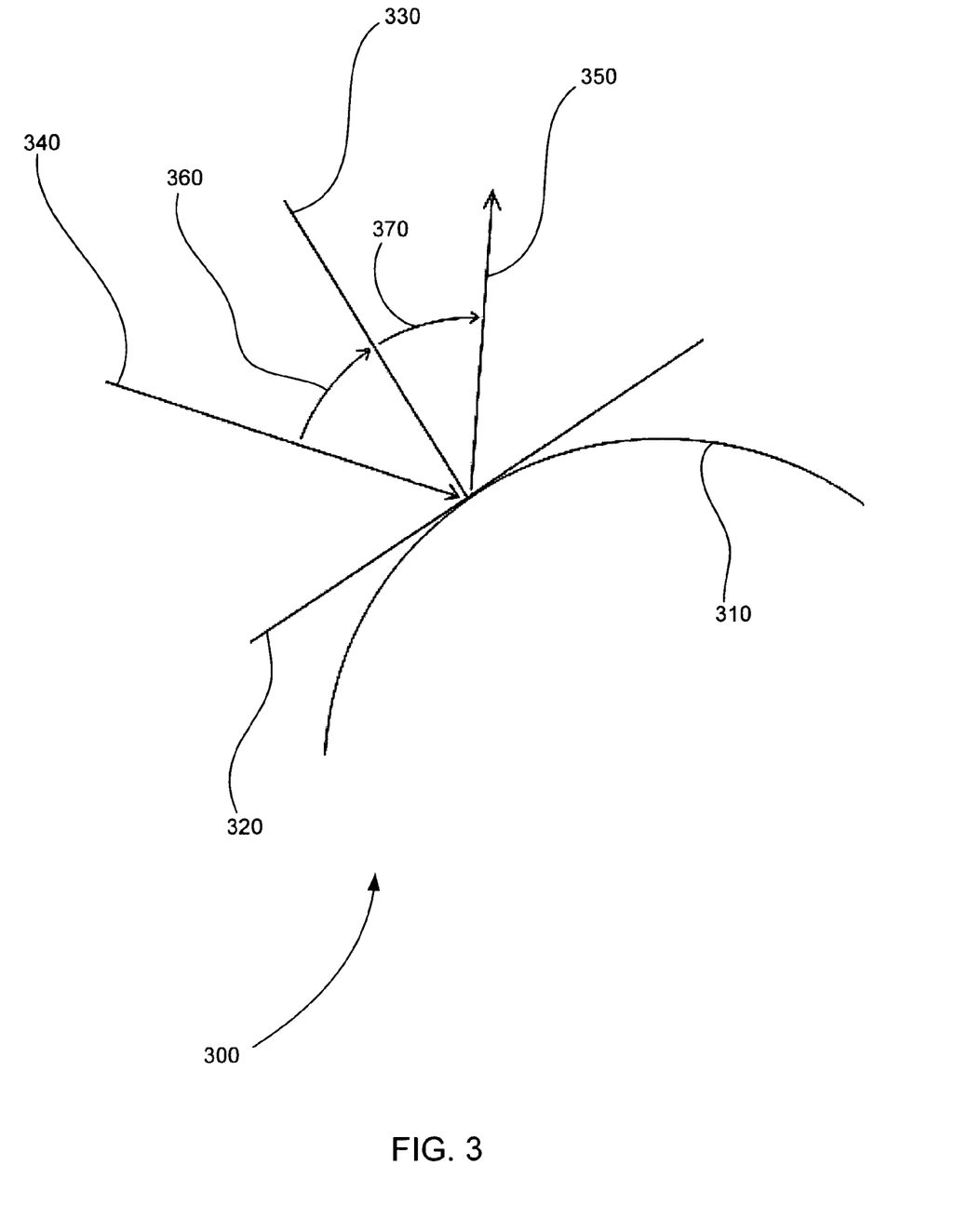
FIG. 3 is an exemplary diagram of reflection from a smooth surface, in accordance with an embodiment of the present invention.

FIG. 3 is an exemplary diagram 300 of reflection from a smooth surface 310, in accordance with an embodiment of the present invention. At the point of intersection with the reflecting object, smooth surface 310 of an eyeball, there is a tangent plane 320. The normal 330 of smooth surface 310 is a vector that is perpendicular in all directions to a tangent of smooth surface 310. Smooth surface 310 causes incident light ray 340 to reflect out as reflecting ray 350. The angle of reflection 370 is equal to the angle of incidence 360.

Each individual cornea or sclera, however, has its own, unique set of surface irregularities that deviate from its ideal shape. Irregularities include large-scale surface warping and regional protrusions, flat spots, ridges and valleys. As noted, the corneal surface must be relatively smooth in order for the eye to form a well-focused image. However the shape of the sclera only needs to be smooth enough for the eye to rotate in the socket without causing irritation. The sclera surface has been observed to have significant surface features, and these features are capable of being used as biometric discriminators.

Figure 4:
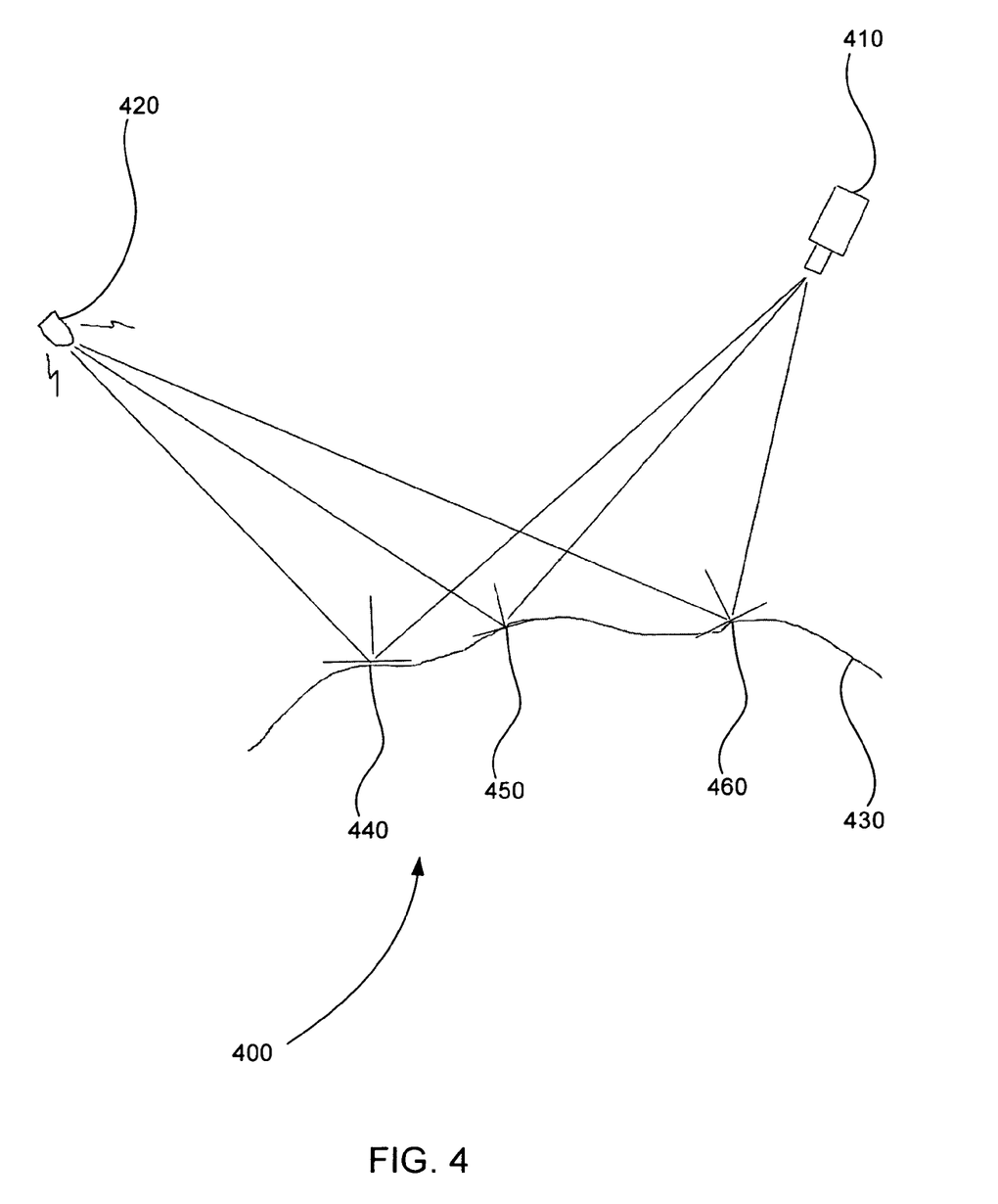
FIG. 4 is a schematic diagram of a system for identifying the irregularities on the surface of an eyeball using a gaze tracking system, in accordance with an embodiment of the present invention.

FIG. 4 is a schematic diagram of a system 400 for identifying the irregularities on the surface of an eyeball using a gaze tracking system 410, in accordance with an embodiment of the present invention.

When using single illuminator 420 to try to verify the presence of a feature point, the vector from the camera of gaze tracking system 410 to that feature point defines the reflecting ray vector. Applying the law of reflection, this in turn defines the vector from the feature point to the source of illumination.

Without an infinite number of illuminators, it is not possible to verify every feature at any given time. System 400 can, however, choose which feature is closest to a possible illumination vector and use that illumination source to attempt to verify the presence of the feature.

In the case of reflections off of the sclera, the surface is only grossly smooth. Therefore there will be multiple points on the surface that will satisfy that law of reflection between illuminator 420 and the camera of gaze tracking system 410.

In FIG. 4, the roughness of surface 430 is highly exaggerated, but it shows how a surface that is not perfectly smooth creates multiple reflections. Surface 430 is the surface of a cornea, a sclera, or the intersection of both a sclera and a cornea, for example. Illuminator 420 produces a broad beam of light rays, within the limits of the beam width, in all directions. These rays are reflected by surface 430. There are multiple surface points 440, 450, and 460 that satisfy the law of reflection between illuminator 420 and the camera of gaze tracking system 410.

At each surface point 440, 450, and 460 there is a specular reflection. Hence, each bright region represents a hill and the darker regions in between represent valleys on the surface of the eye. The bright spots are not precisely the centers of the ridges. In FIG. 4, the reflection at surface point 450 is fairly close to the center of the ridge. However reflections at surface points 440 and 460 are on the shoulders of the ridges.

Figure 5:
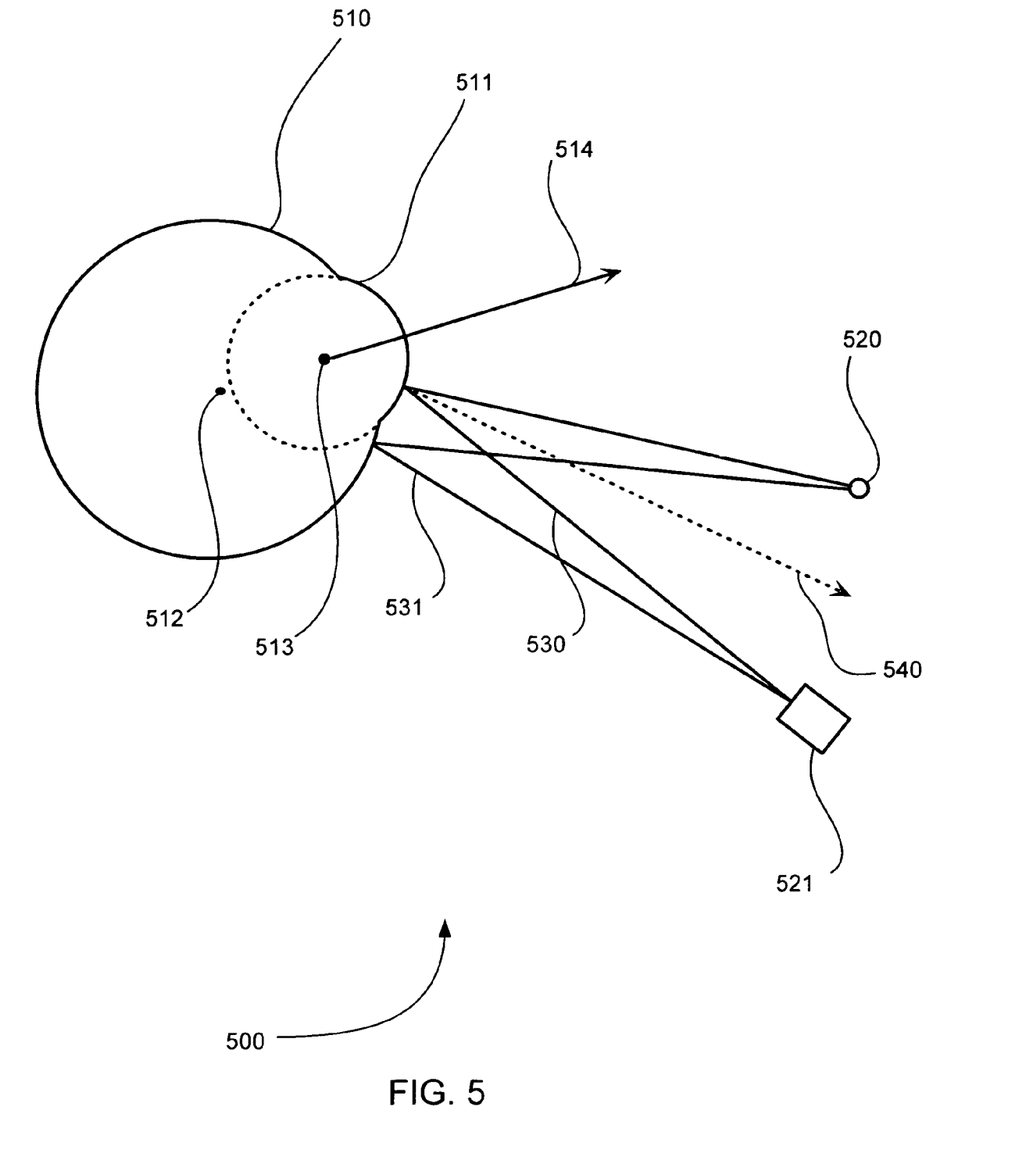
FIG. 5 is a schematic diagram of a system for observing reflections from an eyeball using a gaze tracking system, in accordance with an embodiment of the present invention.

FIG. 5 is a schematic diagram of a system 500 for observing reflections from an eyeball using a gaze tracking system, in accordance with an embodiment of the present invention. FIG. 5 illustrates the optics underlying typical reflections observed in eye images captured by eye-tracking-system cameras. The key outer surfaces of the eye consist of the sclera 510 (i.e., the main body of the eyeball) and the corneal surface 511 (also known as the corneal bulge). Both surfaces are approximately spherical in shape. The centers of the eyeball and corneal spheres are designated 512 and 513, respectively. The orientation of the eye is typically defined by the vector direction of its optic axis 514, which passes through the center 512 of the eyeball sphere and center 513 of the corneal sphere.

Corneal surface 511 spans approximately 90 degrees. Corneal surface 511 "interrupts" a span of approximately 30 degrees of the eyeball sphere. Given that a tear film coats the sclera and cornea, both of these surfaces are reflective.

A video eye tracking system typically has one or more cameras that observe the eye. Camera lens 521 is shown in FIG. 5. The eye tracker also has illuminator 520, or possibly multiple illuminators, that illuminates the eye.

Depending on the orientation 514 of the eye, illuminator 520 may generate several reflections in the eye image captured through eye tracker lens 521. Both a corneal reflection 530 and a scleral reflection 531 are shown in FIG. 5. The reflections occur at points on the surfaces where the angle of incidence from the illuminator equals the angle of reflection to the lens. (As illustrated in FIG. 3, the line that bisects the lines of incidence and reflection is perpendicular to the surface.)

Given that the span of the corneal surface 511 is approximately 90 degrees, there is a range of approximately 90 degrees over which an eye can rotate in which a corneal reflection of the illuminator occurs within the camera image. This range for the occurrence of a corneal reflection, and thus for the ability to measure the direction of gaze, is often referred to as the "gaze-tracking cone". The center axis 540 of the gaze-tracking cone depends on the eye tracker's optical configuration: it is a line from the center of the corneal sphere to a point midway between the eye tracker's illuminator and lens.

While a corneal reflection occurs when the user is looking within the gaze-tracking cone, scleral reflections typically occurs when the user is looking outside a cone of approximately 30 degrees.

If the corneal or scleral surfaces were perfectly spherical, there would be at most a single reflection from each point source of light in the eye tracker illumination system. Furthermore, if the surfaces were convex everywhere, there would only be a single reflection point from each point light source. Typically, the cornea, though it does exhibit significant signature variations in curvature, is convex everywhere. The sclera, however, does frequently exhibit regions of concavity. As illustrated by the optics in FIG. 4 and by the eye image in FIG. 7, these alternations between convexity and concavity lead to multiple reflection points that can be used to identify signature irregularities in the surface. Given that a surface has regions of concavity, it may be recognized by a system with a single, point-source of illumination.

Figure 6:
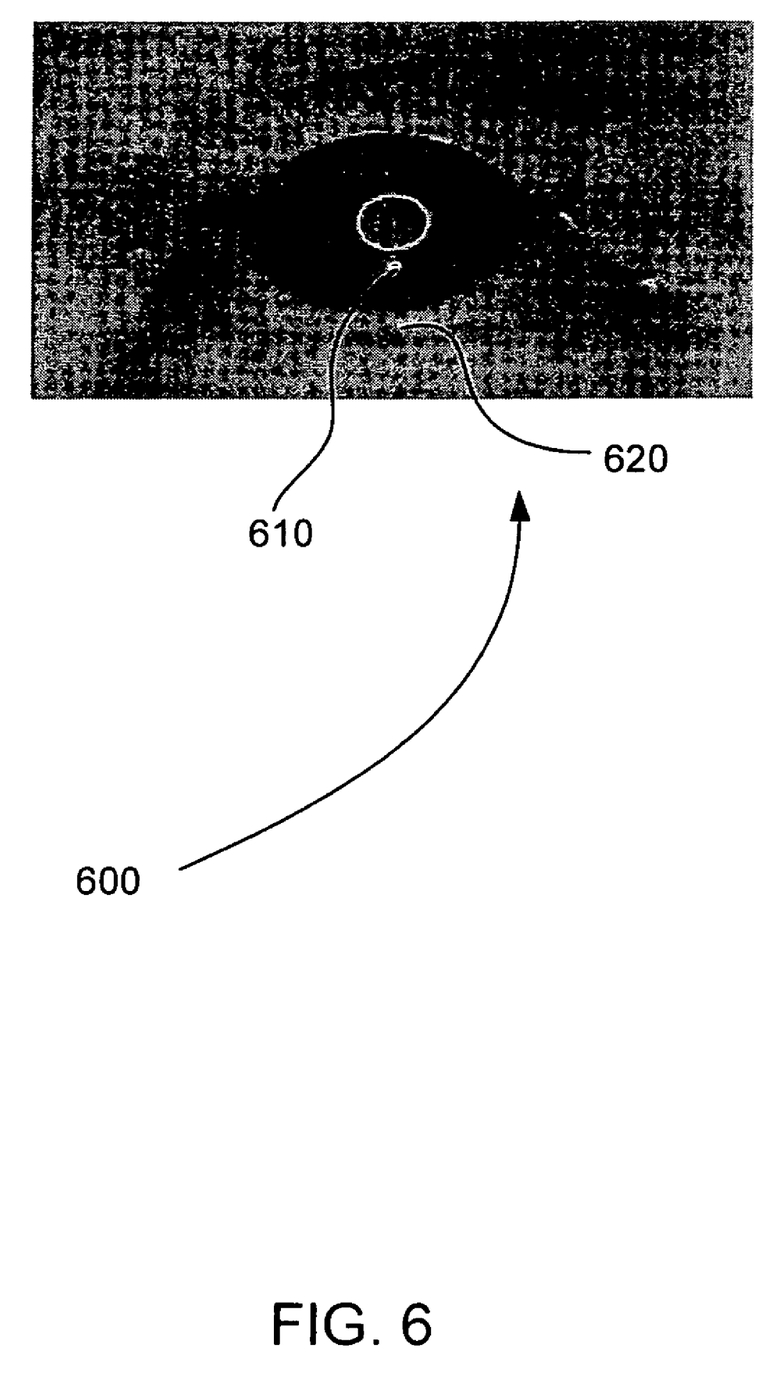
FIG. 6 is an exemplary image of a reflection from a surface point on a cornea and a reflection from a surface point on a sclera as seen by a gaze tracking system, in accordance with an embodiment of the present invention.

FIG. 6 is an exemplary image 600 of a reflection 610 from a surface point on a cornea and a reflection 620 from a surface point on a sclera as seen by a gaze tracking system, in accordance with an embodiment of the present invention.

Figure 7:
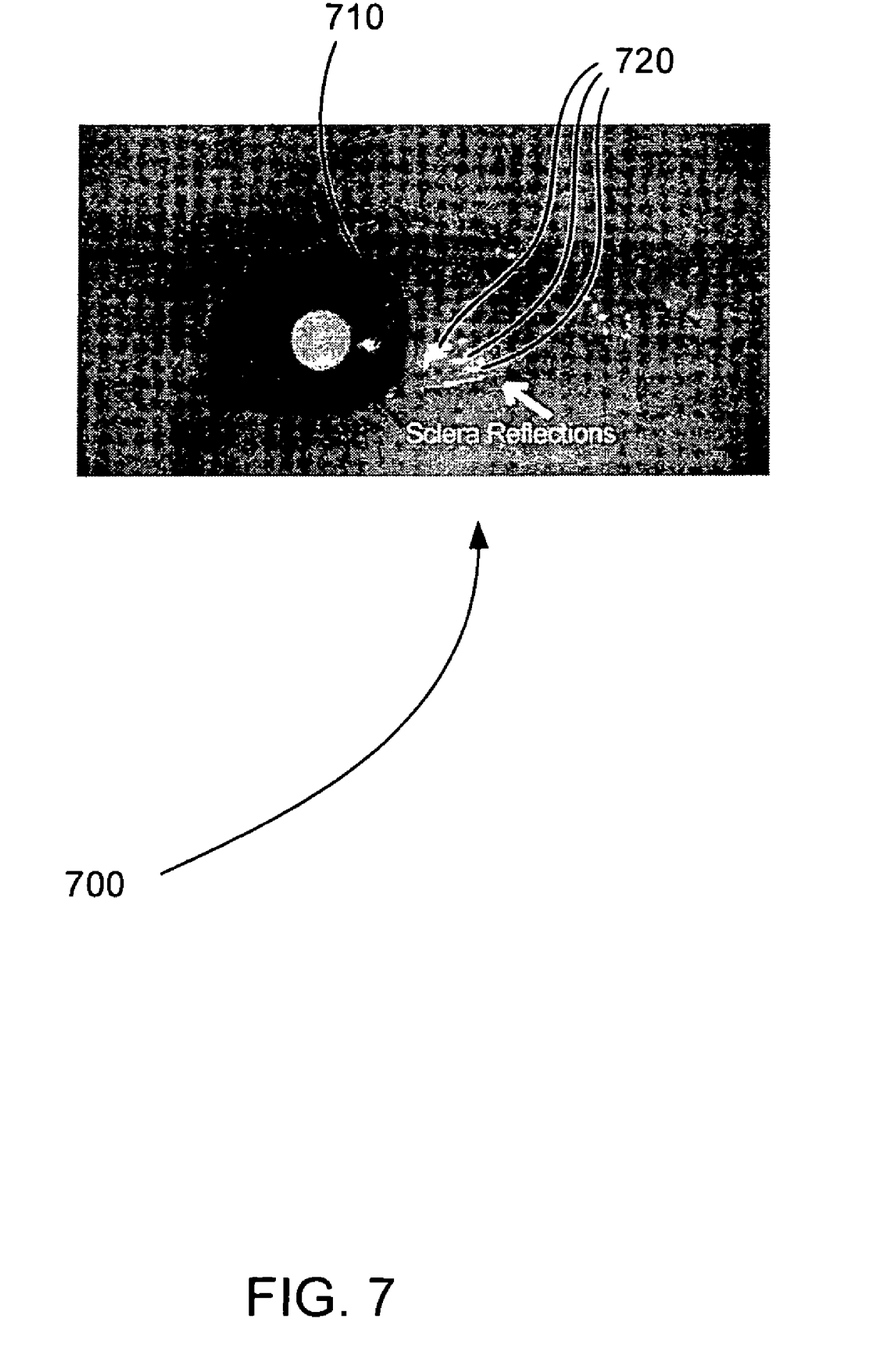
FIG. 7 is an exemplary image of a reflection from a surface point on a cornea and multiple reflections from multiple surface points on a sclera as seen by a gaze tracking system, in accordance with an embodiment of the present invention.

FIG. 7 is an exemplary image 700 of a reflection 710 from a surface point on a cornea and multiple reflections 720 from multiple surface points on a sclera as seen by a gaze tracking system, in accordance with an embodiment of the present invention.

FIG. 6 is the image typically observed by a gaze tracking system. FIG. 7 shows multiple reflections of a tracker's illuminator reflecting off of the sclera. Note that the corneal reflection still reflects off of the corneal bulge. This occurs because both the corneal surface (at the corneal reflection) and the sclera (at the scleral reflections) are perpendicular to the optical axis of the gaze tracker's optical path. Also note that the number of reflections from the surface of the sclera indicates just how rough that surface is and therefore how many features are available on a typical sclera to differentiate individuals. It is the biometric information in the pattern of that roughness that this invention exploits.

Although it can be very useful to identify signature points of concavity in a person's scleral surface, it is highly desirable to be able to measure significantly smaller irregularities that do not involve concavity.

To measure curvature variations where the surface is convex, one solution is to use multiple point light sources and measure variations in the distances between the reflection images. In the preferred embodiment of this invention, an illuminator grid with uniform spacing between multiple point-source illuminators is used to illuminate the eye. If the surface of the eye is perfectly spherical, the surface produces a pattern of reflections that is fully predictable from knowledge of the actual grid pattern and knowledge of the idealized spherical surface. On the other hand, if the surface varies from spherical, the pattern of measured reflector locations differs from the predicted pattern. The pattern shifts are indicative of minor variances in the surface curvature. The system computes the surface curvature profile from these measured variations in the expected reflector pattern.

Cornea Surface Measurement Technology

Figure 8:
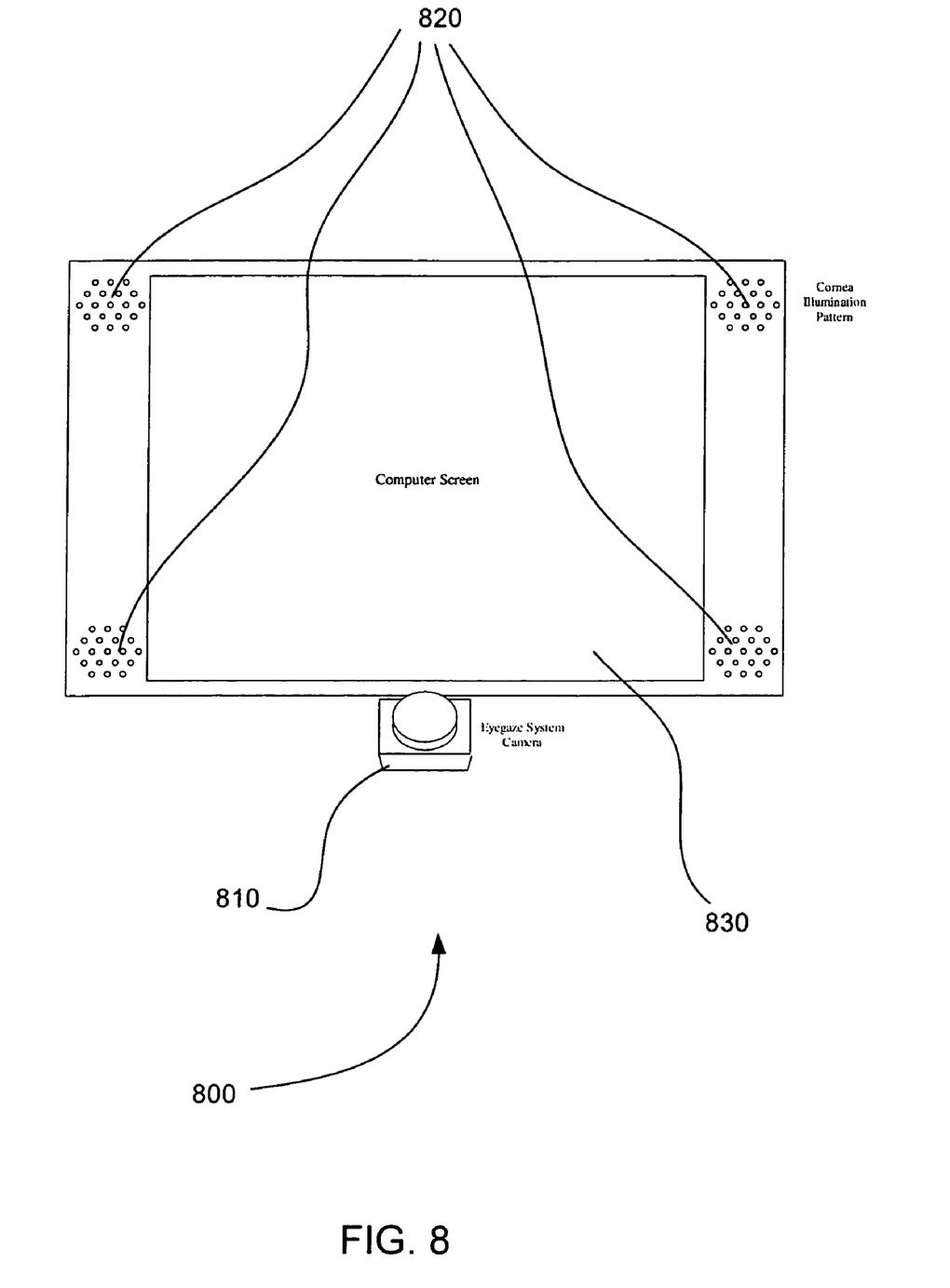
FIG. 8 is a schematic diagram of a system for identifying the irregularities on the surface of an eyeball using a gaze tracking system and one or more grids of illuminators, in accordance with an embodiment of the present invention.

FIG. 8 is a schematic diagram of a system 800 for identifying the irregularities on the surface of an eyeball using a gaze tracking system 810 and one or more grids of illuminators 820, in accordance with an embodiment of the present invention.

To verify the user's identity, system 800 periodically activates one or more grids of illuminators 820 placed around computer screen 830. FIG. 8 shows four sets of illumination patterns constructed from light-emitting diodes. A camera from gaze tracking system 810 captures the grid reflection pattern off the eye's corneal surface.

Cornea verification software of gaze tracking system 810 analyzes the grid-reflection pattern and computes the likelihood that the observed pattern comes from the presumed user's cornea. Due to irregularities in the corneal shape, the captured illumination patterns are slightly warped with respect to the layout of the physical grid. The specific warping of the reflected pattern is, of course, dependent on what portion of the cornea the illumination pattern reflected from. Gaze tracking system 810 provides the eye-orientation data required to determine which portion of the cornea is reflecting the illuminator grid. If the pattern does not match the expectations, the user is deemed to no longer be the user who logged in and the workstation is locked.

Under the assumption that the presumed user identification is correct and gaze tracking system 810 correctly calculated the orientation of the eyeball, the warping in the reflected pattern should match the pattern predicted by user's signature data. Given a match in the observed warping, the user-verification software increases the probability that the user identity is correct. Conversely, if the measured and predicted patterns do not match, the probability of correct user identity is decreased. The factors by which the identification likelihood are increased or decreased are subject to error rate of gaze tracking system 810 and the error rate of the pattern matching, and can be changed to tolerate higher or lower false positive and false negative identifications depending on the security standards governing the workstation.

Figure 9:
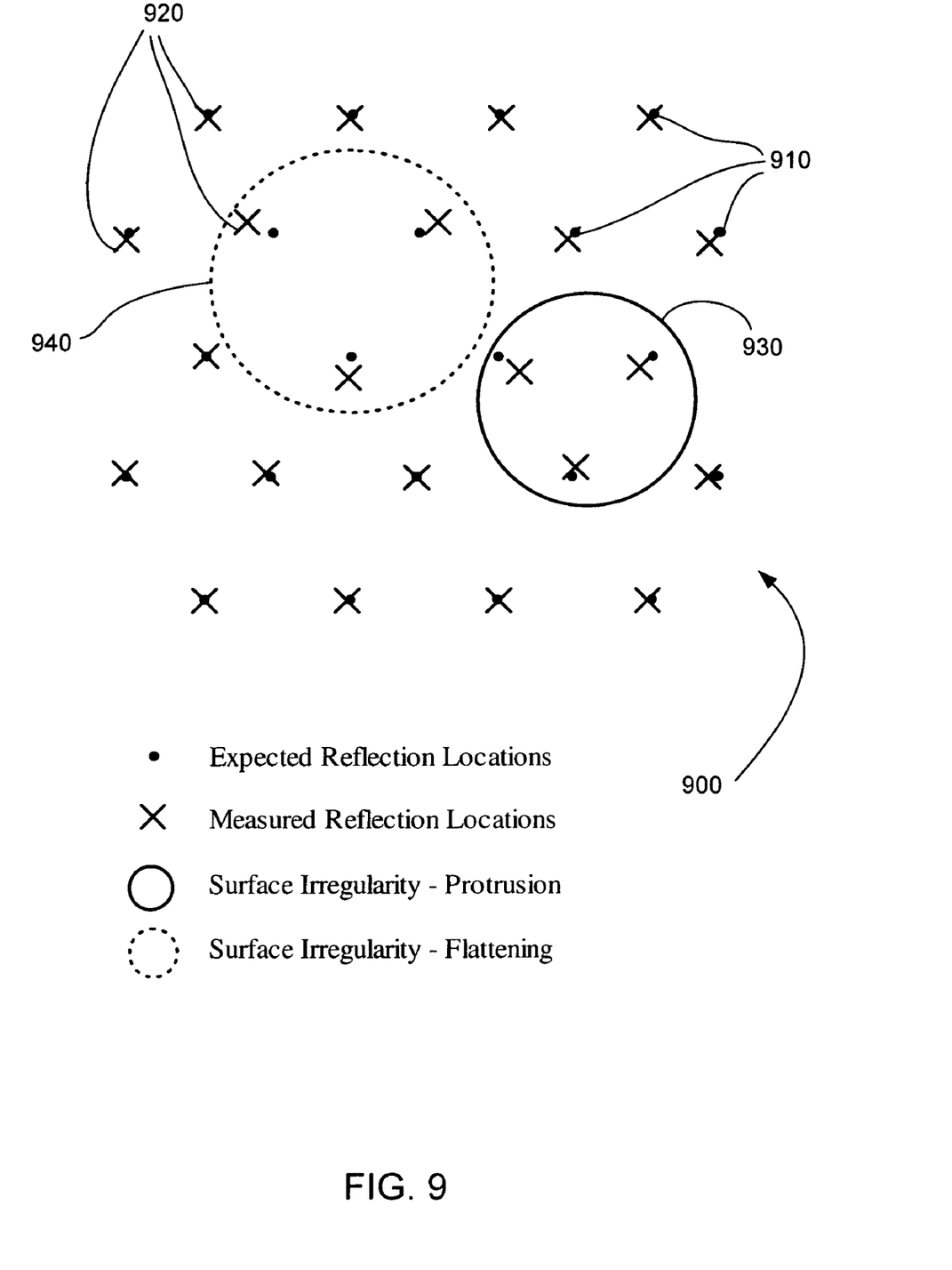
FIG. 9 is a schematic diagram of a reflection grid measured from a camera image, in accordance with an embodiment of the present invention.

FIG. 9 is a schematic diagram of a reflection grid 900 measured from a camera image, in accordance with an embodiment of the present invention. Dots 910 show the expected location pattern based on an idealized spherical reflection surface. The Xs 920 show the locations of the actual reflections measured within the image. In this example, there are two surface irregularities on an otherwise spherical surface. Minor protrusion 930 causes the reflection images to bunch together with respect to the nominal reflector spacing. Conversely, relatively flattened area 940 on the surface, causes the reflection images to spread apart.

Note, the average curvature across either the sclera or cornea is relatively constant. Therefore, from a topological point of view, a relative "protrusion" on a surface comprises regions of both increased and decreased curvature with respect to the average curvature. The curvature in the middle of a protrusion is greater than the average, but there is also a flattened region surrounding the protrusion. Conversely, a flattening consists of a flatter area in the center, surrounded by areas of greater curvature. Therefore, any protrusion or flattening results in regions of both increased and decreased reflection density. In minor protrusion 930, for example, the reflections inside the circle are relatively bunched together, while the separations between these reflections and the ones just outside the circle are larger than average, indicating the flattened annulus that surrounds the protrusion.

To detect surface irregularities, the topography system detects shifts in the measured reflection patterns with respect to the patterns expected from a perfectly spherical surface. Based on the known dimensions and patterns of the illumination grid, and based on the laws of reflection optics, the topography system calculates the magnitude, shape and location of the irregularities required to produce the observed shifts. Knowing the orientation of the eyeball from the eye tracking system, the topography system converts the location of the irregularity within the camera image to its corresponding location on the surface of the eye.

Use in Security Applications

In one possible implementation of a biometric discriminator, a cornea-based identity-verification system coupled to a computer workstation would work as follows.

Enrollment

Prior to being given access to work stations, authorized users are enrolled in the security system. The participant's corneal surface maps are obtained using conventional corneal-topographic equipment. The user's corneal-surface shapes are encoded into signature files. In addition to cornea-shape data, the signature files include calibration data required by the gaze tracking system to calculate the user's eyeball orientation and gaze point.

User Authentication

Once a participant is enrolled, the system locks the workstation until a user's identity is confirmed. The system then allows access to the workstation, while it continually verifies the user's identity. The workstation is locked if the user leaves. Details of the operational work session are as follows:

When a user logs in at the beginning of a session, the cornea-based portion of the security system postulates that the user is who he (or some other identification system) says he is. The system brings up that person's cornea signature data, and it begins to track the user's eyeball position, eyeball orientation, and gaze point based on the presumed user's calibration data.

In the initial login, the user is asked to observe a set of several dots displayed on the computer screen. With the user looking at these locations, the system captures corneal surface topography data on several of the distinctive regions of the user's cornea to begin the authentication process. The number of initial points that the user is asked to view is dependent on the required authentication threshold. The location of the dots is specifically chosen in order to allow the system to observe particular features on the user's eyeball surface.

Once the user passes the authentication threshold, he begins his normal work. As the user's eyes move around the screen during his normal work, the system continually collects topographic data at various locations on the user's cornea. This data is tested against the reference data to continually re-verify that the user is the same individual.

Typically, this continued re-verification requires no interruption to the user's normal work. In the event that insufficient re-verification information is obtained in the normal course of work, the system may require the user to look at specified locations in much the same manner that the original login required.

Biometric Information Content

The type, location, amplitude, orientation and extent of each irregularity on a corneal surface provide significant discriminatory information regarding a person's identity. With 30 bits of discriminatory information, individuals may be identified to one part in a billion.

As discussed above, the original corneal signature for an eye would be derived from corneal-surface maps measured by corneal-topography equipment. For biometric identification purposes, the signature may be described as a set of irregularities.

Below is a table that lists a rudimentary set of candidate features that may be used to characterize each corneal-surface irregularity. The first column in the table lists the type of feature used to describe the irregularity. The second column represents the number of descriptive bits that might be used to characterize the irregularity from the original corneal surface map. The third column indicates the potential number of discriminatory bits extracted by the gaze tracking system to confirm or deny a match between an irregularity in test and reference corneas. Assuming that an average of 8 bits of discriminatory data are available from each irregularity, and assuming that the system identifies 4 irregularities, a total of 32 discriminatory bits would be available for biometric verification.

| Feature Type | Descriptive Bits | Discriminatory Bits | |
|---|---|---|---|
| Location | 16 bits | 4 bits | x, y location of the irregularity on the cornea |
| Amplitude | 6 bits | 2 bits | sign/magnitude of the depression/protrusion |
| Aspect Ratio/ Orientation | 6 bits | 2 bits | aspect ratio/orientation |
| Extent | 6 bits | 2 bits | diameter/length of the irregularity |
| Total | 23 bits | 10 bits | |

Identity-Verification Data Rates

With normal gaze activity, it is anticipated that the system will capture user-verification data at a rate of approximately 2 to 8 bits per second.

On average, people fixate approximately 3 times per second. If the system observes a corneal-surface irregularity once every 5 fixations, and the average irregularity capture provides 5 bits of discriminatory data, the data verification rate is approximately 3 bits per second. At this rate, 10 seconds are required to achieve 30 bits, i.e. one-part-in-billion verification.

With continuous operation, the system will detect a new user within seconds.

Corneal Surface Stability

Corneal surface irregularities are generally small (otherwise we would not see clearly), but they are physically quite stable. Without injury, surgery or disease, the large majority of the irregularities remain appreciably unchanged throughout an individual's adult life. Since the cornea is highly stable, its topography need be measured rarely. For purposes of personal identification, it is expected that a person's corneal topographies need be re-measured less than annually. There is no reason to believe that the corneal or sclera surfaces change any faster than finger prints, which are known to be stable throughout an individual's life.

Non-Disruptive Operation

The cornea-based identity verification system of the present invention does not disrupt the normal work of an authorized user. The user is free to move his head and move his gaze point around the screen at will. The system exploits normal gaze activity to gather relevant surface-shape data from the cornea, so no special activities are required on the user's part. The system captures relevant cornea-surface data as it becomes available.

The corneal-reflection illuminator grids operate in the IR spectrum so their operation is not distracting to the user.

Improving Gazepoint Tracking Accuracy

In addition to providing a source of biometric information on the user, the incorporation of detailed corneal-surface topographies into the gaze tracking system has the potential to improve the system's gaze point tracking accuracies considerably.

The Pupil-Center-Corneal-Reflection (PCCR) method for measuring an eye's angular orientation involves two keys steps. First, the system measures the glint-pupil vector within a video camera image, i.e. the vector distance from the corneal reflection to the pupil center. Second, the system maps the glint-pupil vector into a prediction of the eye's angular orientation (pitch and yaw with respect to the optical axis of the camera). In the gaze tracking system in this embodiment, the glint-pupil-vector-to-eye-orientation mapping, commonly referred to as the calibration model of the eye, is derived from a calibration procedure that effective measures the curvature of the corneal surface. This model assumes that the curvature is uniform and smooth. A significant source of gaze point tracking error arises from differences between this model and the cornea's true geometry.

In an exemplary eyegaze system, the corneal surface model is a single ellipsoidal surface. Five parameters describe the ellipse: the vertical and horizontal radii of curvature, the angle and magnitude of astigmatism, and an elongation parameter indicative of the flattening toward the edges. The system expects these surface parameters to remain constant over the corneal surface. While this 5-parameter ellipsoidal model accounts for all major surface properties of an idealized cornea, it does not currently accommodate local irregularities in the corneal-surface topography. Some irregularities occur naturally, but more significantly, any eyeball that has undergone corrective laser surgery has two curvatures, the original curvature over a significant portion of the cornea, and the corrected curvature over just the portion of the optical path used to form an image (basically the diameter of the pupil in a dark room). Detailed corneal surface topography data will provide a more accurate calibration model than is obtained from the current follow-the-dot calibration procedure.

Figure 10:
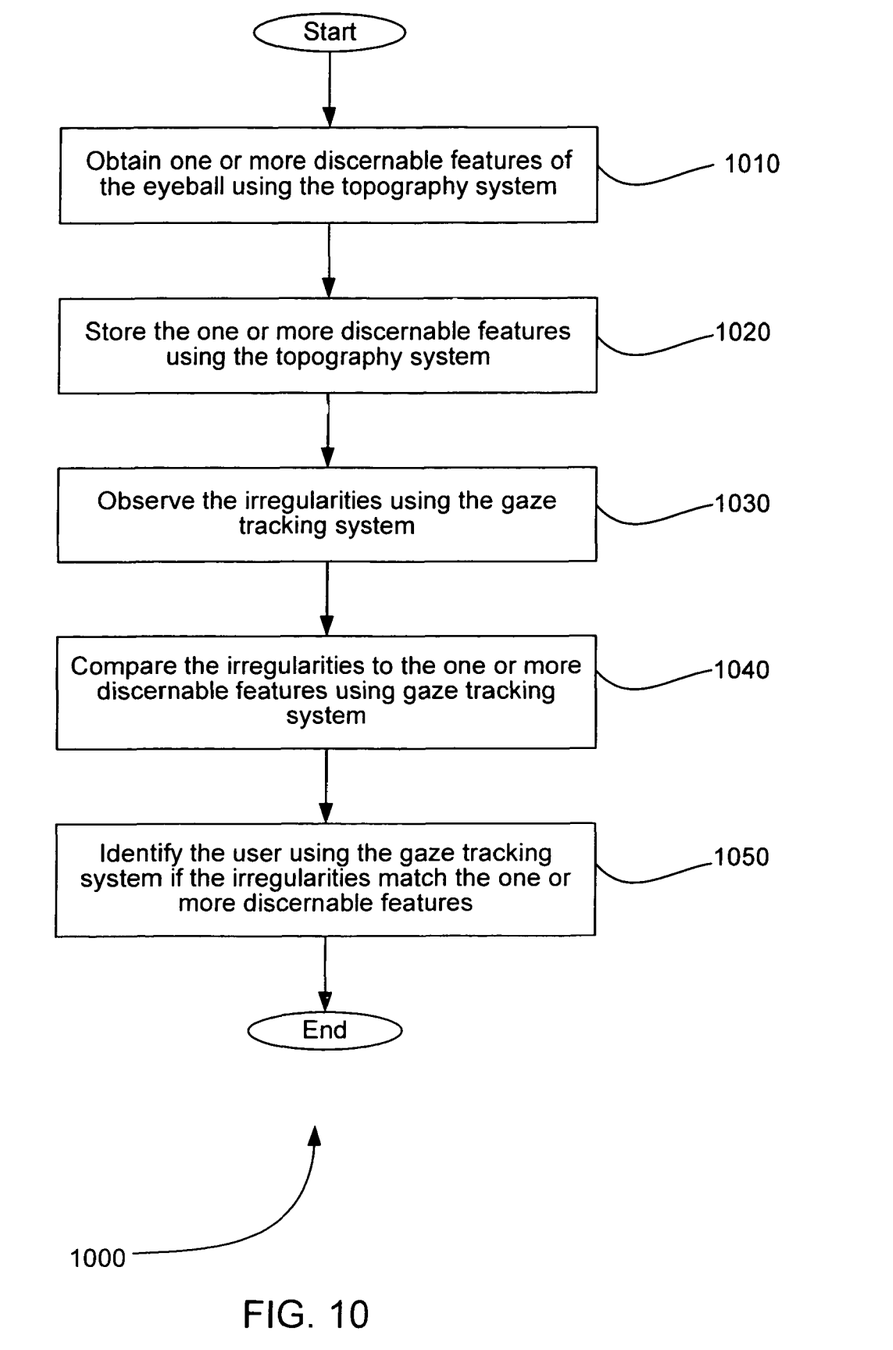
FIG. 10 is a flowchart showing an exemplary method for identifying a user by observing irregularities on the surface of an eyeball of the user using a topography system and a gaze tracking system, in accordance with an embodiment of the present invention.

FIG. 10 is a flowchart showing an exemplary method 1000 for identifying a user by observing irregularities on the surface of an eyeball of the user using a topography system and a gaze tracking system, in accordance with an embodiment of the present invention.

In step 1010 of method 1000, one or more discernable features of the eyeball are obtained using the topography system.

In step 1020, the one or more discernable features are stored using the topography system.

In step 1030, the irregularities are observed using the gaze tracking system.

In step 1040, the irregularities are compared to the one or more discernable features using the gaze tracking system.

In step 1050, the user is identified using the gaze tracking system if the irregularities match the one or more discernable features.

Further examples of the present invention are as follows.

A first example is a method for biometric discrimination which includes a gaze tracking system that compares the measurements from the gaze tracking system with a biometric database.

A second example is a method that is substantially similar to the first example in which the gaze tracking system includes a method for measuring corneal surface irregularities.

A third example is a method that is substantially similar to the second example and includes measuring the surface of the sclera.

A fourth example is a method for biometric discrimination which includes a gaze tracking system that compares the measurements from the gaze tracking system with a biometric database and includes additional illumination sources.

A fifth example is a method that is substantially similar to the fourth example and includes arranging the additional illumination sources in a defined pattern.

A sixth example is a method for biometric discrimination which includes a gaze tracking system that compares the measurements from the gaze tracking system with a biometric database and uses any optical property of the eyeball as a biometric discriminator.

A seventh example is a system for biometric discrimination including a gaze tracking system that uses corneal topography as one of the calibration parameters of the system.

An eighth example is a system for biometric discrimination including a gaze tracking system that uses corneal topography as one of the calibration parameters of the system.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for continually verifying the identity of an eye observing a computer screen, comprising:
   a biometric database that stores topographic data about the eye that determines an identity of the eye;
   a light source that illuminates the eye;
   a camera that images the eye and one or more reflections of the light source from the eye as the eye observes a screen over time; and
   a processor in communication with the camera and the biometric database that
      calculates an angular orientation of an optical axis of the eye from an image of the eye and the one or more reflections of the light source from the eye,
      identifies an irregularity on a surface of the eye from the one or more reflections of the light source in the image,
      determines the location of the irregularly on the eyeball from the angular orientation, and
      compares the irregularity to the topographic data in the biometric database using the location to verify an identity of the eye.

2. The system of claim 1, wherein the topographic data comprises corneal data.

3. The system of claim 1, wherein the topographic data comprises scleral data.

4. The system of claim 1, wherein the topographic data is obtained using a corneal topography system.

5. The system of claim 1, wherein the topographic data is obtained using the illuminator, the camera, and the processor during an enrollment period.

6. The system of claim 1, wherein the topographic data comprises a set of irregularities.

7. The system of claim 1, wherein the light source comprises an infrared light source.

8. The system of claim 1, wherein the light source comprises a single illuminator.

9. The system of claim 1, wherein the light source comprises a grid of illuminators.

10. The system of claim 1, wherein the camera comprises a video camera.

11. The system of claim 1, wherein the processor further locks access to a workstation that comprises the screen if the identity of the eye is not verified.

12. A method for continually verifying the identity of an eye observing a computer screen, comprising:
   storing topographic data about an eye that determines an identity of the eye using a biometric database;
   illuminating the eye using a light source;
   imaging the eye and one or more reflections of the light source from the eye as the eye observes a screen over time;
   calculating an angular orientation of an optical axis of the eye from an image of the eye and the one or more reflections of the light source from the eye using a processor;
   identifying an irregularity on a surface of the eye from the one or more reflections of the light source in the image using the processor;
   determining the location of the irregularly on the eyeball from the angular orientation; and
   comparing the irregularity to the topographic data in the biometric database using the location to verify an identity of the eye using the processor.

13. The method of claim 12, wherein the topographic data comprises corneal data.

14. The method of claim 12, wherein the topographic data comprises scleral data.

15. The method of claim 12, wherein the topographic data is obtained using a corneal topography method.

16. The method of claim 12, wherein the topographic data is obtained using the illuminator, the camera, and the processor during an enrollment period.

17. The method of claim 12, wherein the topographic data comprises a set of irregularities.

18. The method of claim 12, wherein the light source comprises an infrared light source.

19. The method of claim 12, wherein the light source comprises a single illuminator.

20. The method of claim 12, wherein the light source comprises a grid of illuminators.

21. The method of claim 12, wherein the camera comprises a video camera.

22. The method of claim 12, wherein the processor further locks access to a workstation that comprises the screen if the identity of the eye is not verified.

* * * * *